US00PP34508P2

(12) United States Plant Patent
Hansen

(10) Patent No.: US PP34,508 P2
(45) Date of Patent: Aug. 16, 2022

(54) **X *MANGAVE* PLANT NAMED 'PRAYING HANDS'**

(50) Latin Name: ***Manfreda* x *Agave* hybrid**
Varietal Denomination: Praying Hands

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 74 days.

(21) Appl. No.: 17/300,432

(22) Filed: Jun. 29, 2021

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 5/12
See application file for complete search history.

*Primary Examiner* — Kent L Bell

(57) ABSTRACT

A new and unique X *Mangave* plant named 'Praying Hands' characterized by habit that is rounded, mounded, with lanceolate foliage. The overall shape is globose as it develops and becomes tear-drop to pyriform-shaped in maturity. The numerous, dark, olive-green, lanceolate leaves have large, firm, deep wine-colored apical mucro, and few, small, widely-spaced marginal teeth. Leaf bases are outwardly and then become upwardly in the middle and strongly introrse toward the apices. Leaves are dark olive-green with small light wine spotting and thin deep wine-colored margins. The new plant is suitable as a potted houseplant plant, as a container plant for the patio or garden and for the garden or planted in the landscape.

2 Drawing Sheets

Botanical classification: *Manfreda* x *Agave* hybrid.
Variety denomination: 'Praying Hands'.

STATEMENT REGARDING PRIOR DISCLOSURES UNDER 37 CFR 1.77(b)(6)

The first non-enabling public disclosure of x *Mangave* 'Praying Hands' were on Mar. 2, 2020 as a brief description and photograph on two websites operated by Walters Gardens, Inc. and subsequently listed with a photograph and description in the "Walters Gardens 2020-2021 Catalog" first distributed on May 20, 2020. Information for this website and catalog, and plants for this sale were obtained from the inventor. The first sales disclosure of the new plant was on Apr. 5, 2021 by Walters Gardens, Inc. No plants of x *Mangave* 'Praying Hands' have been sold, in this country or anywhere in the world as of this filing, nor has any disclosure of the new plant been made, more than one year prior the filing date of this application, and such disclosure within one year was either derived directly or indirectly from the inventor.

BACKGROUND OF THE INVENTION

The present invention relates to the new and distinct X *Mangave* plant, X *Mangave* 'Praying Hands' hybridized on Jul. 7, 2014 by the inventor at a wholesale perennial nursery in Zeeland, Mich., USA as a cross between 'Bloodspot' (not patented) as the female or seed parent and a proprietary selection of *Agave ocahui* identified only as PDN #7 (not patented) as the male or pollen parent. Through trials at the same nursery the plant was referred to by the code 14-74-4. The new plant has been successfully asexually propagated initially in 2019 by core shoot tip and later by shoot tip tissue culture at the same nursery in Zeeland, Mich. These asexual propagation systems have been found to produce stable and identical plants that maintain all the unique characteristics of the original plant in successive generations.

BRIEF SUMMARY OF THE INVENTION

X *Mangave* 'Praying Hands' differs from its parents as well as all other *Manfreda, Agave* and x *Mangave* known to the applicant. The most similar x *Mangave* cultivars known to the inventor are: 'Sponge Paint' U.S. Plant Pat. No. 32,070, 'Pineapple Express' U.S. Plant Pat. No. 28,613, 'Lavender Lady' U.S. Plant Pat. No. 29,194 and 'Aztec King' U.S. Plant Pat. No. 32,151.

'Sponge Paint' has a more glaucous, oblanceolate to rhombic foliage with large marginal teeth, less globe-like habit with foliage apices that are more extrorse or more divergent. 'Pineapple Express' has a more horizontal habit with leaf apices that are more extrorse, leaves that are a more strongly mahogany spotted and finely marginally toothed. 'Lavender Lady' has more rhomboidal foliage that is more extrorse, finely marginally toothed with smaller apical mucro and a more glaucous purplish color. 'Aztec King' has a more outright and larger habit with lighter silver-grey leaves with more intense purple spotting, small marginal teeth and larger apical mucro.

The female parent, 'Bloodspot' has a more horizontal habit with foliage apices that are more extrorse, stronger mahogany spotting with small marginal teeth, more glaucous and smaller apical mucro. The male parent is slower growing with a more rounded habit, the foliar apices that are more introrse and leaves lack the darker spotting.

The new plant, 'Praying Hands', is unique from all of these *Agave*, X *Mangave* and *Manfreda* known to the inventor by the following combined traits:

1. Rounded, mounded, with overall habit initially globose and becoming tear-drop to pyriform-shaped in maturity with about 100 leaves;
2. Dark olive-green foliage is lanceolate with few, small, widely-spaced, short, marginal teeth and long, stiff, wine-colored apical mucro;
3. Leaves have deep wine-colored thin margins and matching apical mucro;
4. Leaf bases are outwardly and distally begin curling around and pointing toward center axis;
5. Moderate growth rate.

BRIEF DESCRIPTION OF THE DRAWINGS

The photograph of the new plant demonstrates the overall appearance of 'Praying Hands' including the unique traits as a four-year-old plant grown in a full-sun trial garden with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
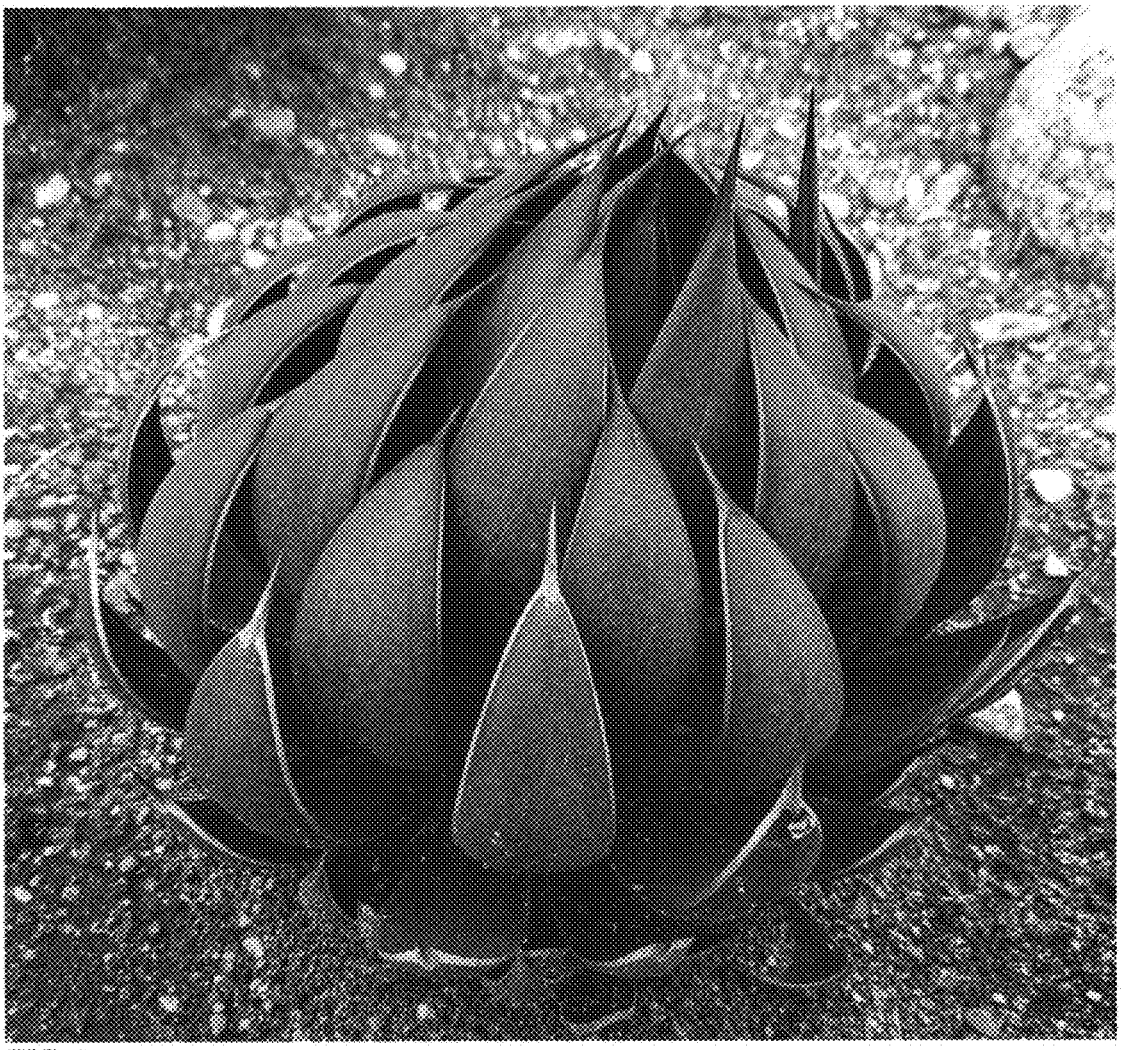
FIG. 1 shows the habit of the new plant from the side.
Figure 2:
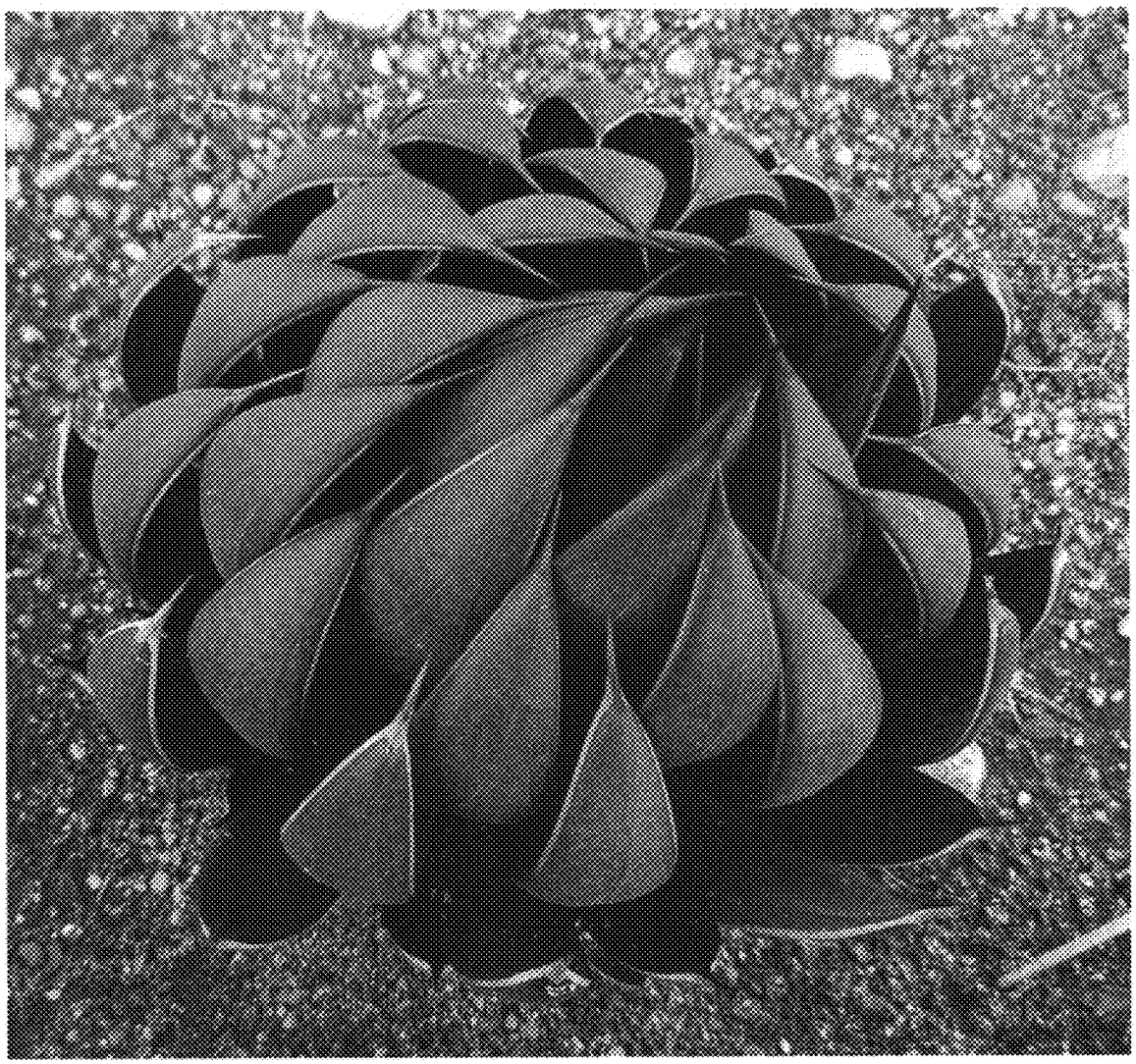
FIG. 2 shows the habit of the new plant from above.

The following descriptions and color references are based on the 2015 edition of The Royal Horticultural Society Colour Chart except where common dictionary terms are used. The new plant, X *Mangave* 'Praying Hands', has not been observed under all possible environments. The phenotype may vary slightly with different environmental conditions, such as temperature, light, fertility, moisture and maturity levels, but without any change in the genotype. The following observations and size descriptions are of four-year-old plants in a commercial wholesale greenhouse and in a full-sun display garden in Zeeland, Mich. with supplemental water and fertilizer as needed.

Botanical classification: x *Mangave* hybrid (*Manfreda* x *Agave*);

Parentage: 'Bloodspot' as the female or seed parent and *Agave ocahui* PDN #7 as the male or pollen parent;

Propagation: Sterile plant tissue culture;

Time to initiate roots from tissue culture: About 28 days;

Growth rate: Moderate;

Crop time: About 20 to 24 weeks to finish during lengthening spring days from an established 25 mm tissue culture plug to a 65 mm diameter container;

Rooting habit: Fleshy, lightly branching, with roots up to 35 cm long and typically 3.0 mm diameter;

Root color: Nearest RHS 155D;

Plant shape and habit: Succulent herbaceous perennial with basal rosettes of up to about 100 fleshy leaves emerging outwardly from short stem and arching upwardly and introrse toward apices, producing a symmetrical, rounded, globose, mound;

Plant size: Foliage height about 26.0 cm tall from soil line to the top of the leaves and 30.0 cm wide at about 12 cm above soil level;

Foliage description: Lanceolate; simple; sarcous; glabrous; fibrous; moderately lustrous adaxial and abaxial; margins smooth in distal two-thirds and dentate with small short teeth in proximal one-third; apex acute with long firm mucro; base truncate, sessile, clasping; flat surface; curved outwardly near base and upwardly and introrse toward apex;

Leaf size: To about 20.0 cm long, about 3.5 cm wide in the widest portion about one-third from base, basal portion flared to about 4.0 cm wide at attachment, about 2.0 cm wide about 3.0 cm from base and 1.5 cm thick at base;

Marginal teeth: Flattened top to bottom; very small, about 0.5 mm long and 1.0 mm wide; proximally concentrated, to about 5.0 to 15.0 mm apart; distally void;

Foliage fragrance: None observed;

Leaf blade color:

*Adaxial* (*lower ultraviolet exposure*).—Young between RHS 138B and RHS N138B without significant spotting; mature between RHS 137B and RHS N138B without significant spotting.

*Abaxial* (*lower ultraviolet exposure*).—Young between RHS 138B and RHS 137B without significant spotting; mature between RHS N137C and RHS N138B with subtle lightly-blushed spotting of nearest RHS N187A.

*Adaxial* (*higher ultraviolet exposure*).—Young and mature nearest RHS N138B distally and the base between RHS 145A and RHS 146D, without significant spotting.

*Abaxial* (*higher ultraviolet exposure*).—Young and mature nearest RHS 138A with small spots to about 6 mm diameter of between RHS N186B and RHS N187B.

*Marginal teeth color*.—Young adaxial and abaxial between RHS 166A and RHS 175A, while leaf still enrolled nearest RHS 187A, mature adaxial between RHS 166A and RHS 176A, mature abaxial between RHS 198C and RHS NN155D.

Mucro: Firm; sharp; straight, about 21.0 mm long and 4.0 mm across at base;

Mucro color: Young variable, between RHS 181A, RHS 183A and RHS 187B; mature between RHS 198C and RHS NN155D;

Petiole: Sessile;

Veins: Parallel; not distinct;

Flower description: Flowers not yet observed;

Fruit: Not yet observed;

Seed: Not yet observed;

Disease resistance: x *Mangave* 'Praying Hands' has not been observed to be resistant or susceptible to diseases common to other x *Mangave* beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental X *Mangave* plant named 'Praying Hands' as herein described and illustrated.

* * * * *